United States Patent [19]
Paulous et al.

[11] Patent Number: 6,103,462
[45] Date of Patent: Aug. 15, 2000

[54] RAPID SINGLE-CYCLE ASSAY FOR HUMAN IMMUNODEFICIENCY VIRUS TYPE-1 DRUG RESISTANCE

[75] Inventors: Sylvie Paulous, Sarcelles; Pierre Charneau, Paris; Vèronique Zennou, Creteil; Francois Clavel, Paris, all of France

[73] Assignee: Institut Pasteur, Paris, France

[21] Appl. No.: 09/129,790

[22] Filed: Aug. 6, 1998

Related U.S. Application Data

[60] Provisional application No. 60/087,335, May 29, 1998.
[51] Int. Cl.[7] .................................................. C12Q 1/70
[52] U.S. Cl. ................................ 435/5; 435/6; 435/235.1
[58] Field of Search ............................ 435/5, 4, 6, 235.1, 435/320.1

[56] References Cited

PUBLICATIONS

Kellam et al. "Recombinant Virus Assay: a Rapid, Phenotypic Assay for Assessment of Drug Susceptibility of Human Immunodeficiency Virus Type 1 Isolates", *Antimicrobial Agents and Chemotherapy*, vol. 38, No. 1 (Jan. 1994), pp. 23–30.

Harrigan et al. "Significance of Amino Acid Variation at Human Immunodeficiency Virus Type 1 Reverse Transcriptase Residue 210 for Zidovudine Susceptibility", *Journal of Virology*, vol. 70, No. 9 (1996), pp. 5930–5934.

*Primary Examiner*—Jeffrey Stucker
*Attorney, Agent, or Firm*—Finnegan, Henderson, Farabow, Garrett & Dunner, L.L.P.

[57] ABSTRACT

An in vitro, single cycle, recombinant virus assay (RVA) for determining inhibition of HIV replication by a protease inhibitor comprises transfecting a human epithelial cell line with amplified HIV protease sequences of an HIV virus; an HIV, envelope defective, molecular clone having a complete deletion of its protease coding sequence; and a plasmid containing HIV envelope coding sequence under the control of a promoter for phenotypic complementation of the envelope defective molecular clone. The transfected cells are cultured in the presence of a protease inhibitor to produce a testable stock of infectious particles that can be used to infect indicator cells containing an indicator gene without amplification of the infectious particles prior to infecting the indicator cells. Accumulation of indicator gene product is a measure of inhibition of HIV replication by the protease inhibitor.

18 Claims, 3 Drawing Sheets

SEQUENCE LISTING

<160> NUMBER OF SEQ ID NOS: 8

<210> SEQ ID NO 1
<211> LENGTH: 23
<212> TYPE: DNA
<213> ORGANISM: primer

<400> SEQUENCE: 1
gctaattttt tagggaagat ctg                              23

<210> SEQ ID NO 2
<211> LENGTH: 23
<212> TYPE: DNA
<213> ORGANISM: primer

<400> SEQUENCE: 2
ggcaaatact ggagtattgt atg                              23

<210> SEQ ID NO 3

-continued

```
<211> LENGTH: 23
<212> TYPE: DNA
<213> ORGANISM: primer

<400> SEQUENCE: 3
tttttaggga agatctggcc ttc                                              23

<210> SEQ ID NO 4
<211> LENGTH: 23
<212> TYPE: DNA
<213> ORGANISM: primer

<400> SEQUENCE: 4
ggagtattgt atggattttc agg                                              23

<210> SEQ ID NO 5
<211> LENGTH: 18
<212> TYPE: DNA
<213> ORGANISM: primer

<400> SEQUENCE: 5
ccctctcaga agcaggag                                                    18

<210> SEQ ID NO 6
<211> LENGTH: 20
<212> TYPE: DNA
<213> ORGANISM: primer

<400> SEQUENCE: 6
tgggccatcc attcctggct                                                  20

<210> SEQ ID NO 7
<211> LENGTH: 10
<212> TYPE: DNA
<213> ORGANISM: primer

<400> SEQUENCE: 7
ctagacgcgt                                                             10

<210> SEQ ID NO 8
<211> LENGTH: 8
<212> TYPE: DNA
<213> ORGANISM: primer

<400> SEQUENCE: 8 cgacgcgt                                                                8
```

RAPID SINGLE-CYCLE ASSAY FOR HUMAN IMMUNODEFICIENCY VIRUS TYPE-1 DRUG RESISTANCE

CROSS-REFERENCE TO RELATED APPLICATION

This regular U.S. patent application claims the benefit of U.S. provisional patent application No. 60/087,335, filed May 29, 1998, the entire disclosure of which is relied upon and incorporated herein by reference.

BACKGROUND OF THE INVENTION

This invention relates to a method for determining HIV susceptibility to protease inhibitors.

Treatment of the Human Immunodeficiency Virus type 1 (HIV-1) infection by antiretrovirals can lead to the selection of virus variants with decreased susceptibility to these agents. Near complete inhibition of HIV replication in vivo by triple combinations of reverse transcriptase inhibitors (RTIs) and of protease inhibitors (PIs), now often termed highly active antiretroviral therapy (HAART), is believed to significantly prevent emergence of resistance. However, in many patients treated by such drug combinations, HIV resistance to both RTIs and PIs can gradually develop, which appears to be mostly the case for patients in which the antiviral combination has failed to achieve a complete block of viral replication. In such patients, optimally active alternative treatment regimens need to be found, which will require careful measurement of HIV susceptibility to antiretroviral drugs. In addition, since antiviral combination therapy needs to be optimized to ensure the best long-term antiviral response, it could be essential to monitor HIV susceptibility profiles to antiretrovirals before the onset of therapy.

The monitoring of HIV resistance to antiretrovirals can be performed by genotypic analysis of the protease (PR) and of the reverse transcriptase (RT) coding regions of viral genomes carried in the plasma of infected patients. Nevertheless, the number of mutations in PR or in RT that are able to affect HIV susceptibility to a growing number of antiviral molecules is increasing considerably. Hence, the observed combinations of mutations, which are certainly an important marker of the evolution of resistance in the course of the treatment, cannot give precise indications on the actual level of susceptibility or resistance of the studied virus. Instead, only phenotypic assays, which directly measure inhibition of virus replication by antivirals in culture, can provide a quantitative assessment of resistance.

Several of the currently used phenotypic resistance assay systems examine the susceptibility of virus isolates obtained by coculture of patient blood cells with donor primary peripheral blood mononuclear cells (PBMCs). These methods require several rounds of virus growth in primary donor cells for virus amplification, titration, and subsequent testing in the presence of the drugs. As a consequence they are costly and highly time-consuming.

More recently, an innovative technique, the recombinant virus assay (RVA), based on previous observations showing that deletions in transfected retroviral genomes could be repaired by homologous recombination, was proposed by Kellam and Larder. In this system, PCR-amplified viral RT sequences from patient plasma were cotransfected with a RT-deleted infectious molecular clone of HIV yielding a recombinant virus carrying the RT sequences of patient plasma virus. Since the molecular clone used for recombination was initially obtained from a laboratory-adapted HIV-1 strain, the recombinant virus could be conveniently tested on established cell lines instead of primary cell cultures.

Several versions of the RVA have been developed for HIV-1 susceptibility testing, which have yielded EC50 values that correlate well with corresponding HIV-1 RT or PR genotypes. However, in these recombinant systems, as well as in the PBMC assay, production of a testable stock of infectious particles requires amplification and titration of virus produced by exponential growth in lymphocytic cells, a step that requires cumulative rounds of viral replication and promotes genetic drift of the virus. Since several mutations able to confer resistance to RTIs or PIs have been shown to reduce the replicative capacity of the virus and to be selected against during drug-free HIV replication, there exists a need in the art for a susceptibility assay for HIV that would only require one step of virus replication.

SUMMARY OF THE INVENTION

This invention aids in fulfilling this need in the art by providing an in vitro, single cycle, recombinant virus assay (RVA) for determining inhibition of HIV replication by a protease inhibitor. The method comprises transfecting a human epithelial cell line with: (1) Amplified HIV protease sequences of an HIV virus to be assayed for resistance to the protease inhibitor; (2) an HIV, envelope defective, molecular clone for recombination, wherein the molecular clone has a complete deletion of its protease coding sequence and an envelope deletion so that no HIV envelope is expressed by the HIV molecular clone; and (3) a plasmid containing VSV-G envelope coding sequence under the control of a promoter for phenotypic complementation of the HIV, envelope defective, molecular clone. The resulting transfected cells are contacted with the protease inhibitor and cultured to repair the protease coding sequence by homologous recombination between the HIV molecular clone and the amplified HIV protease sequences, and to produce a testable stock of infectious particles by coexpression of the protease-repaired HIV molecular clone and the VSV-G envelope coding sequence, such as a VSV-G envelope coding sequence. Indicator cells containing an indicator gene are contacted with the testable stock of infectious particles without amplification of the infectious particles prior to infecting the indicator cells. The indicator gene is expressed in the indicator cells, and accumulation of indicator gene product is determined as a measure of HIV replication. The susceptibility of the recombinant virus to protease inhibitors is determined by contacting transfected cells with serial dilutions of the inhibitor, allowing to calculate the concentration of inhibitor able to inhibit 50 or 90% of virus infectivity [IC50 and IC90].

This invention provides a single-cycle version of RVA for testing HIV resistance to protease inhibitors. Similar to the previously described RVA systems, the assay of the invention uses recombination of PCR-amplified HIV sequences from plasma with a deleted HIV molecular clone. In one embodiment of the invention, cotransfection can be performed in human epithelial cells (e.g., HeLa cells) that are subsequently treated with serial dilutions of protease inhibitors, since the inhibitory action of these compounds is only perceptible upon treatment of virus-producing cells, yielding a small stock of testable virus particles. The resulting particle stocks can be subsequently tested for infectivity on a HeLa-derived P4 cell line, which allows precise and quantitative titration of HIV on the basis of a single round of replication.

To increase the sensitivity of the test and to make sure that replication of the tested particles in the P4 cells is limited to a single cycle, in a preferred embodiment of the invention, the HIV envelope coding sequences can be removed from the HIV plasmid clone, and phenotypic complementation of the envelope ensured by coexpression of an exogenous viral envelope protein, such as VSV-G envelope glycoprotein.

Overall, the results obtained with the assay of the invention match the genotypes of the tested viruses and the treatment history of the corresponding patients. Since the assay of the invention is particularly rapid (5 days on average, not including the PCR), the assay is useful for routine monitoring of HIV drug susceptibility in treated HIV-infected patients.

BRIEF DESCRIPTION OF THE DRAWINGS

This invention will be described in greater detail with reference to the drawings in which:

FIG. 1 depicts a procedure leading to production of recombinant virus carrying protease sequences from patient plasma;

FIG. 2 shows the effects of increasing doses of two protease inhibitors (SQV and IDV) on the infectivity of recombinant particles produced with protease sequences from two patients, obtained for each patient before protease inhibitor therapy and after protease inhibitor escape;

FIG. 3 shows the results of a further evaluation of HIV-1 cross-resistance to protease inhibitors using the single-cycle recombinant assay of the invention conducted in four (4) patients that had followed distinct treatment regimens;

DETAILED DESCRIPTION OF PREFERRED EMBODIMENTS

Figure 1A:
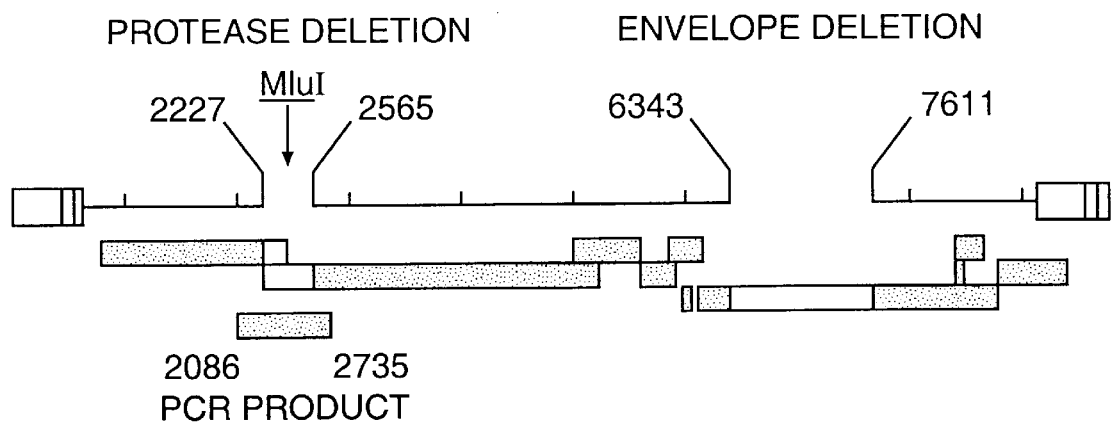
FIG. 1A shows a physical map of patient-derived viral nucleic acid and deletions created in that viral nucleic acid to provide sequences for production of recombinant virus.

This invention provides a new phenotypic assay for the evaluation of Human Immunodeficiency Virus type 1 (HIV-1) resistance to protease inhibitors. The assay is derived from the recombinant virus assay (RVA) technique (Kellam and Larder, 1994), which is based on recombination between a PCR product: representing HIV sequences from patient plasma virions and a deleted laboratory HIV molecular clone, following their cotransfection into mammalian cells.

In contrast with all previously described HIV phenotypic assays, the assay of the invention does not require amplification of virus production through cumulative rounds of virus replication in lymphoid cells. Instead, virus produced by the transfected cells in the presence of different concentrations of protease inhibitors can be directly tested for infectivity on HIV-susceptible HeLa-derived indicator cells on the basis of a single round of viral replication. The indicator cells can carry an HIV-inducible LacZ gene that allows rapid and quantitative HIV titration by a simple calorimetric method. To increase the sensitivity of the system and to further ensure that HIV replication in the indicator cells is limited to a single cycle, the virions are deprived of HIV envelope and pseudotyped by the VSV-G envelope glycoprotein, which markedly enhances single cycle infectivity of HIV particles.

Overall, the assay of the invention can be performed in less than one week. The lack of requirements for serial virus passage and amplification implies that no genetic drift of the tested viral sequences can take place during testing. The assay allows reliable and reproducible assessment of HIV resistance to protease inhibitors, with good correlations between the measured IC50/IC90 values and the corresponding protease genotypes. This assay is useful for monitoring of HIV susceptibility to antiretroviral agents in the course of the treatment of infected patients.

In the assay of this invention, replication of the tested virus is divided in two distinct steps, requiring two distinct cell systems. In the transfected HeLa cells, following transfection and repair of the deleted genomes by homologous recombination, the HIV genome is expressed and viral particles are assembled and released. Conversely, the indicator P4 cells are the site of "early" steps of HIV replication: entry, reverse transcription, nuclear import of viral DNA, integration, and gene expression up to the production of sufficient amounts of the Tat transactivator for the accumulation of detectable amounts of the indicator Lac-Z gene product, $\beta$-galactosidase.

The consequence of the separation of the HIV replicative cycle in two parts is that testing for resistance to protease inhibitors according to this invention requires drug treatment of the transfected HeLa cells, while testing for reverse transcriptase inhibitors requires drug treatment of the indicator P4 cells. Conversely, in assays that rely on full replication of HIV in lymphoid cells, the format of drug treatment of the indicator cultures is similar for protease inhibitors and reverse transcriptase inhibitors. The requirement for two different drug treatment formats in the assay of the invention is outweighed by its other advantages.

Preliminary resistance measurements on viruses that have developed resistance to protease inhibitors have been obtained using the assay of the invention. The results are presented as IC90 values, which, given the sensitivity of the assay and the range of the dilutions of antiviral drugs used, gave the most reproducible and reliable results. Clearly, these results show that the IC90 values of the studied viruses are consistent both with the virus genotypes and with the therapeutic histories of the corresponding patients. The assay of the invention is useful, in general, for quantitative assay for drug resistance.

The assays of the invention can be included in large-scale clinical trials aimed at evaluating the best therapeutic strategies in patients failing antiretroviral therapy of HIV infection. Since an optimal antiretroviral impact has proven essential to preventing treatment failure and emergence of resistance, such assays are also useful in determining optimal drug combinations before the onset of the treatment in naive patients.

The invention is described in greater detail below with reference to the inhibition of HIV replication by a protease inhibitor, but it will be understood that the invention can also be employed in an assay for determining HIV susceptibility to reverse transcriptase inhibitors. In this event, two modifications may be made. The proviral plasmid should be deleted in the reverse transcriptase coding sequences, and the reverse transcriptase-PCR primers should be designed to amplified the reverse transcriptase coding region from plasmatic virus patients. Secondly, P4 target cells, and not producer cells of the type used for determining inhibition of HIV replication by protease inhibitors, can be treated with a gradient of reverse transcriptase inhibitor compound of interest.

In this regard, while the invention is described below with reference to known protease inhibitors, it will be understood that the method of the invention can be practiced with any type of compound to determine whether it has protease inhibition activity. Thus, a compound or composition of interest, such as one having unknown activity, can be substituted for the known protease inhibitor in the assays described below.

Similarly, while the invention is described with reference to HIV-1, it will be understood that the invention is equally applicable to the determination of inhibition of HIV replication by a protease inhibitor on HIV-2. In this event, the corresponding plasmids and primers should be specific for HIV-2.

Further, while the invention is described in detail below with reference to plasmid pNLME, it will be understood that other HIV molecular clones can be employed for recombination. Indeed, any proviral infectious plasmid clone can be employed in practicing this invention. The clone can be provided with an RT deletion using conventional techniques.

In a preferred embodiment of the invention, the HIV envelope coding sequence in the HIV molecular clone used for recombination is env defective. That is, envelope is not expressed by the recombinant virus. Viruses carrying a defective envelope gene should not make any detectable amounts of envelope, should not be infectious, and should be such that the molecular clone can easily be trans-complemented with another envelope, such as VSV-G.

The invention is described below with reference to human epithelial cells. HeLa cells were chosen for their transfectability, although it will be understood that any equivalent cells can be employed in the invention. HeLa cells give excellent virus yields following transfection. Transfection can be carried out with established cell lines.

The assay of the invention also employs an indicator cell. The invention is described with reference to the use of P4 cells, although other indicator cells are suitable. P4 cells have been found to be suitable for use in the assay of the invention because they have no beta-galactosidase background activity, which might otherwise interfere with the quantitative determinations made possible by the invention. See J. MOL. BIOL. (1994), Charneau et al. Other indicator cell lines can be employed, such as cell lines engineered using, for example, the REV systems.

Similarly, the invention is described with reference to an indicator gene in the indicator cell. The P4 cells contain the gene encoding beta-galactosidase. Other indicator genes, such as luciferase, green florescent protein (GFP), or alkaline phosphatase can also be employed.

When the HIV molecular clone used for recombination contains an envelope deletion, cells transfected with the clone should be phenotypically complemented by another source of envelope protein. While a variety of complementing systems can be employed, the VSV-G envelope glycoprotein has been found to be the most efficient envelope for the present assay. The VSV-G envelope glycoprotein expression vector is pMD.G. This vector is described in *Blood*, 1997, vol. 90[3], pages 952–957, Gallardo, H. F. et al. See also, Akkina et al., J. Virol. 70:2581–85. Other envelopes from other viruses can be employed to coat (pseudotype) HIV particles. For example, envelope of amphotropic murine retroviruses can be employed.

In the examples that follow, calcium phosphate mediated transfection was employed. It will be understood, however, that other chemical or physical techniques can be employed. For example, lipofection and electroporation are suitable alternative techniques that are well known in the art.

Cells have been transfected with increasing amounts of protease PCR product. There is an increase in the efficiency of recombination. The goal, however, is not to make as much virus as possible, but rather to determine drug resistance even with small amounts of PCR product, such as, from clinical samples.

The HIV envelope coding sequence employed for phenotypic complementation is under the control of a promoter. Any inducible or regulatable promoter is suitable for this purpose.

In order to enhance the recombination efficiency following cotransfection, linearization of the plasmid at the site of the protease deletion is advantageous. This embodiment of the invention is described with reference to the insertion of a unique MluI site in place of the protease deletion. It will be understood, however, that other unique restriction sites can be employed. The site that is utilized should be absent from the recombinant molecular clone used for recombination.

Finally, it will be apparent that the invention has broad application. For instance, the assay can be adapted for any type of compound if the proviral plasmid clone is deleted in the appropriate region, such as integrase or envelope. A suitable complementing sequence can be provided in these circumstances.

Figure 1B:
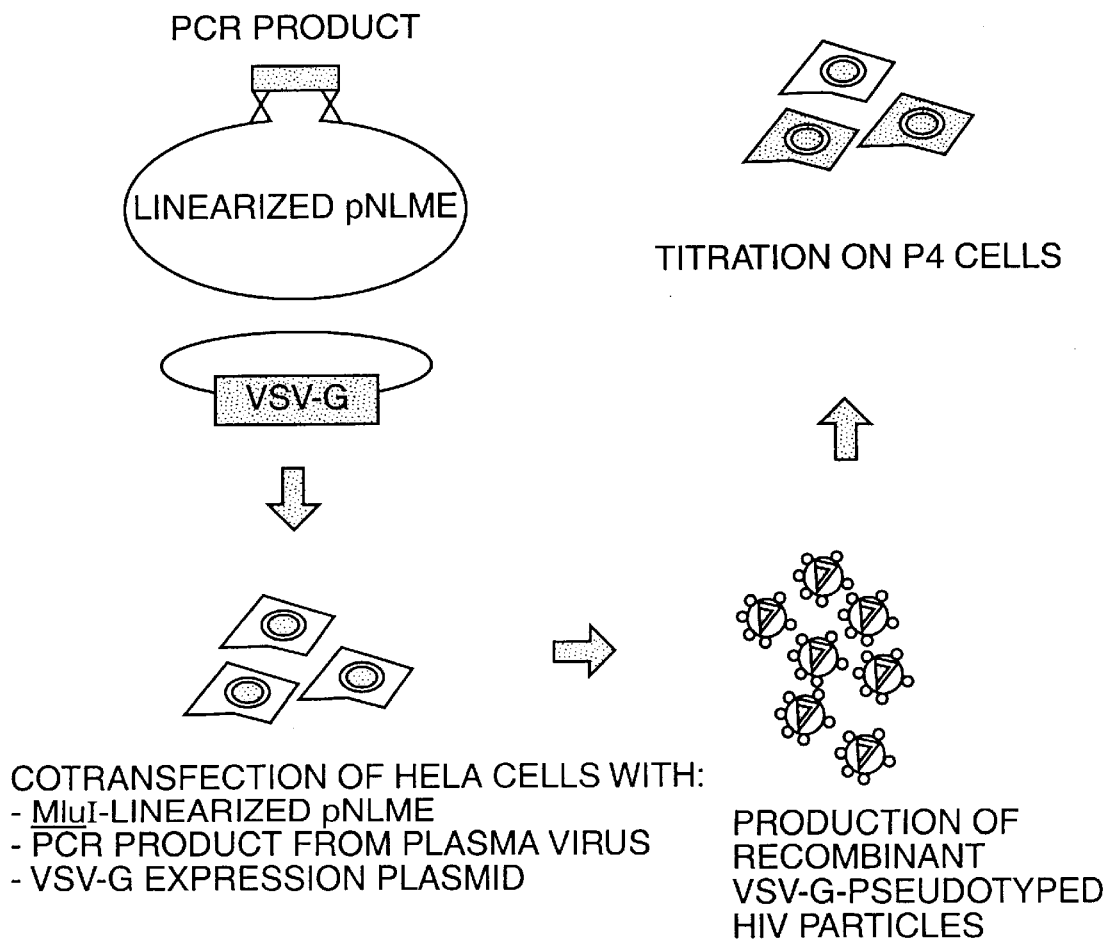
FIG. 1B shows a process for incorporating patient-derived viral sequences into recombinant viruses.
Figure 2A:
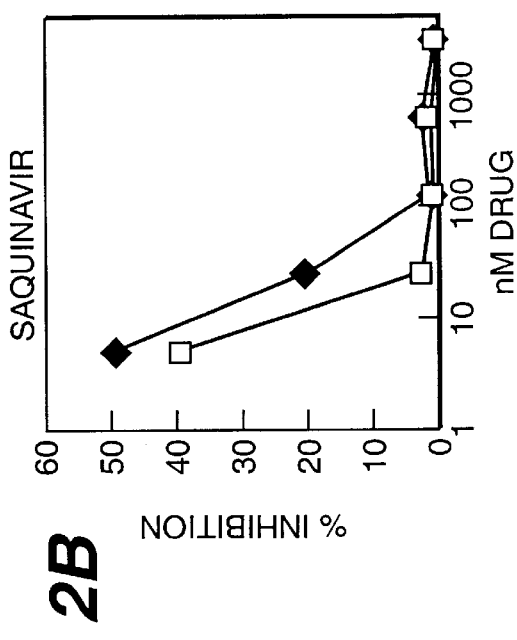
FIG. 2A depicts the effects of increasing doses of indinavir on the infectivity of recombinant particles produced with protease sequences derived from a patient ("patient A")
Figure 2B:
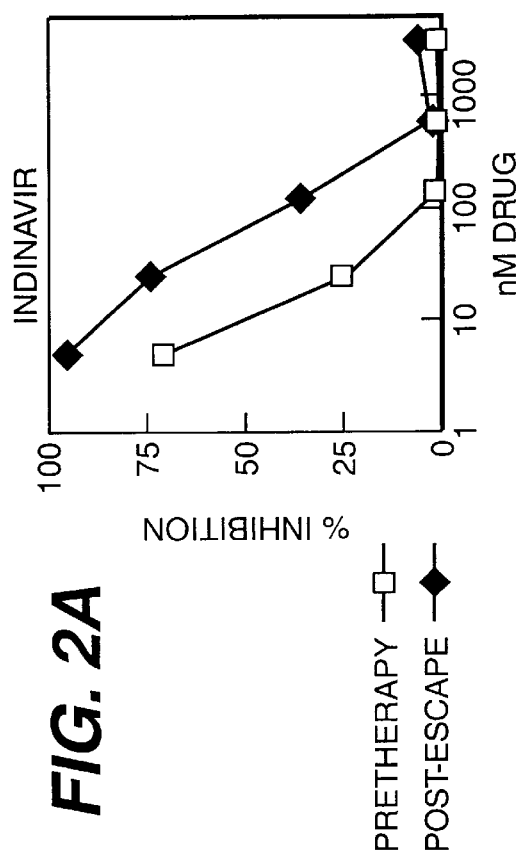
FIG. 2B depicts the effects of increasing doses of saquinavir on the infectivity of recombinant particles produced with protease sequences derived from a patient ("patient A")
Figure 2C:
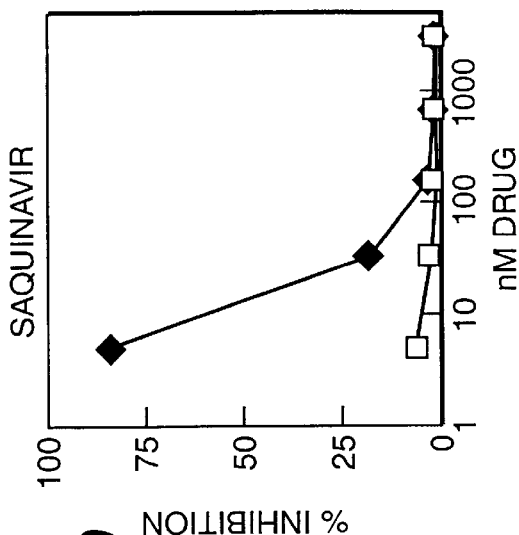
FIG. 2C depicts the effects of increasing doses of indinavir on the infectivity of recombinant particles produced with proteases sequences derived from a patient ("patient B")
Figure 2D:
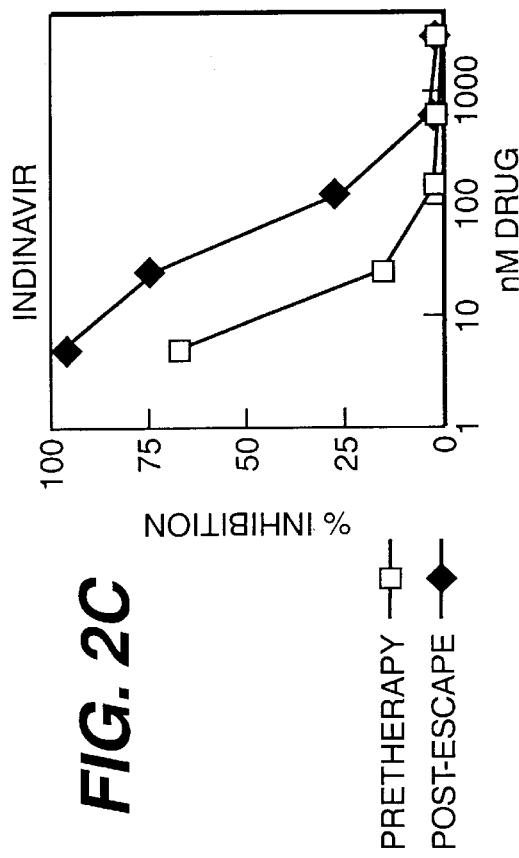
FIG. 2D depicts the effects of increasing doses of saquinavir on the invectivity of recombinant particles produced with protease sequences derived from a patient ("patient B")
Figure 3B:
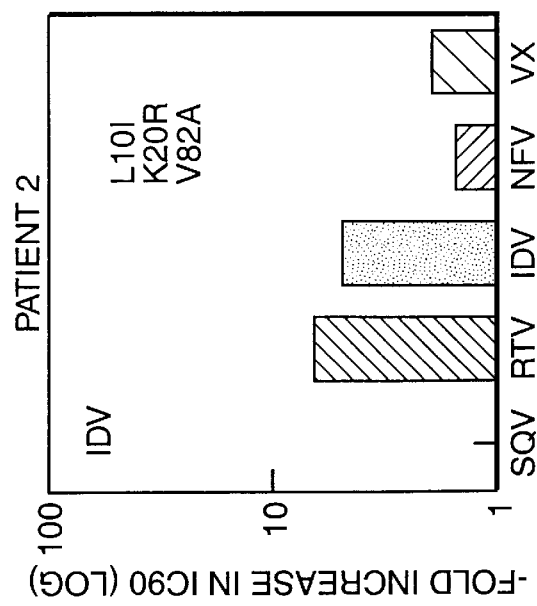
FIG. 3B shows the results of HIV-1 cross-resistance to various protease inhibitors after treatment of a patient with indinavir (IDV)
Figure 3D:
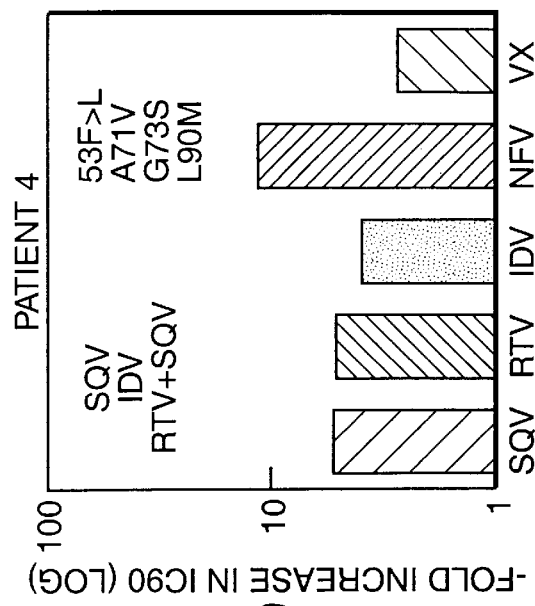
FIG. 3D shows the results of HIV-1 cross-resistance to various protease inhibitors after successive treatments of a patient with saquinavir (SQV), indinavir (IDV), and an association of ritonavir (RTV) and saquinavir (SQV).
Figure 3A:
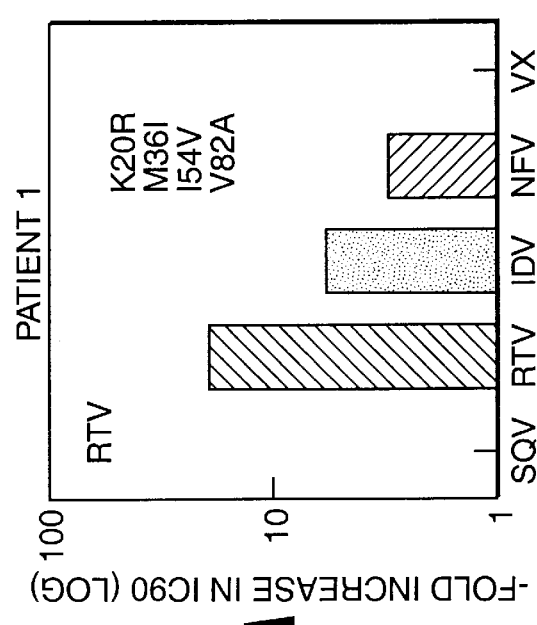
FIG. 3A shows the results of HIV-1 cross-resistance to various protease inhibitors after treatment of a patient with ritonavir (RTV)
Figure 3C:
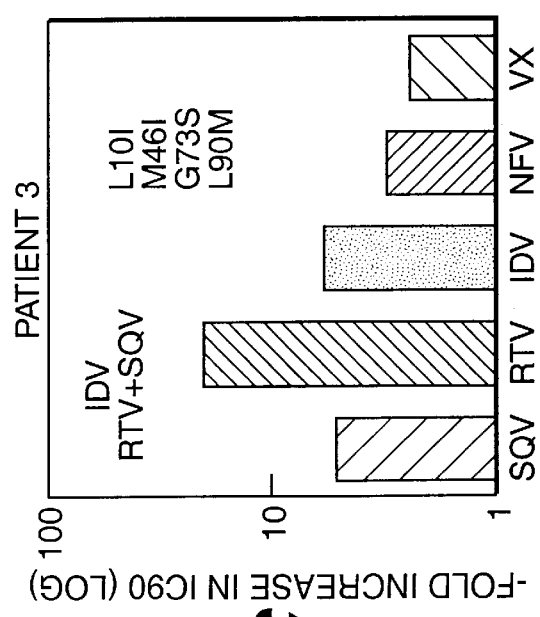
FIG. 3C shows the results of HIV-1 cross-resistance to various protease inhibitors after treatment of a patient with indinavir (IDV) followed by an association of ritonavir (RTV) and saquinavir (SQV)

Production of pseudotyped recombinant viruses that are competent for a single cycle of replication A procedure leading to production of recombinant virus carrying protease sequences from patient plasma is depicted in FIG. 1. Plasmid pNLME contains two separate deletions: the first deletion corresponds to the protease coding sequence, while the second deletion involves the env gene.

The boundaries of the protease deletion match precisely those of the protease coding sequence, which will ensure that infectious viruses obtained by homologous recombination between pNLME and a segment of DNA spanning the protease coding region would always contain at least the whole protease sequence from the latter.

A linker containing a unique MluI site was inserted in place of the protease deletion, allowing simple linearization of the plasmid at this deletion site. It has been previously shown that recombination efficiency following such cotransfections is markedly enhanced by linearization of plasmid at the site of the deletion. The size of the protease PCR product used for recombination with plasmid pNLME is 639 bp, a segment that overlaps the protease deletion in pNLME by 166 bp upstream of the protease coding sequence and by 175 bp downstream. It will be understood, however, that other sizes of the fragment overlaps can be employed as long as the overlap is sufficient to insure homologous recombination. Typically, overlaps of about 100 nucleotides or more are suitable for homologous recombination. Smaller overlaps can reduce the rate of recombination. Larger overlaps can reduce the efficiency of the PCR reaction.

The envelope deletion in plasmid pNLME ensures that the genome of the recombinant virus is not competent for replication unless phenotypically complemented by another source of envelope protein. In the preferred system of the invention, this complementation is provided by cotransfection of the VSV-G envelope glycoprotein. Since expression of the VSV-G protein is limited to the cotransfected cells, the resulting pseudotyped particles are only competent for a single cycle of replication, thereby preventing the spread of the virus in the indicator cell cultures. Furthermore, VSV-G pseudotyped HIV-1 particles display a significantly enhanced single-cycle infectivity when compared to wild-type particles.

Effect of protease inhibitors on the single-cycle infectivity of pseudotyped recombinant virus The protease of retroviruses exerts its function during or shortly after assembly and release of viral particles. That is, protease inhibitors are only active in cells that produce and assemble virus, rather than on cells that harbor the initial steps of virus replication. Consequently, testing susceptibility of HIV-1 to protease inhibitors in the system described above requires treatment of the particle-producing transfected cell cultures (Nascimbeni et al., manuscript in preparation).

Accordingly, separate HeLa cultures in 24-well plates were transfected with equal amounts of a mixture of MluI-linearized pNLME, protease PCR product from patient plasma (molar ratio of plasmid:PCR product=1), and pVSV-G plasmid. Twenty four hours after transfection, the cultures were washed and treated with increasing concentrations (5 to 3125 nM) of Saquinavir (SQV) or Indinavir (IDV) for 24 hours. The resulting particle suspensions were then titrated on P4 cells.

FIG. 2 shows the effects of increasing doses of SQV and IDV on the infectivity of recombinant particles produced with protease sequences from two patients, obtained for each patient before protease inhibitor therapy and after protease inhibitor escape. For all tested recombinant viruses, increasing protease inhibitor concentrations in the transfected cultures resulted in a clear and gradual inhibition of single-cycle particle infectivity. Moreover, for both protease inhibitors tested, the extent of the inhibition of infectivity was clearly different in pretherapy and post-escape viruses.

Pretherapy virus from patient A carried a wild-type protease sequence, while post-escape virus, obtained after 6 months of SQV therapy followed by 9 months of IDV therapy, carried mutations L10I, A71V, G73S, V82A, and L90M. As shown on FIG. 2, a marked difference in susceptibility to SQV and to IDV was observed between the recombinant pretherapy and post-escape viruses.

Patient B was treated by Ritonavir (RTV), and before the introduction of Ritonavir, the virus carried mutations M36I and A71V, known to participate in HIV-1 resistance to several protease inhibitors. Following RTV escape, the protease was found to carry mutations K20R, M36I, M46L, I54V, A71V, and V82A. Again, a clear susceptibility difference between the pretherapy and post-escape viruses was visible both for IDV and SQV. However, presumably because of the two baseline protease mutations, pretherapy virus from this patient was clearly less susceptible to SQV than pretherapy virus from patient A.

Measurement of HIV-1 resistance and cross-resistance to protease inhibitors by single-cycle recombinant assay The single-cycle recombinant assay of the invention can be used for HIV-1 protease inhibitor susceptibility testing in no longer than five days: transfection is performed on day 1; treatment of the transfected cells by protease inhibitors on day 2; infection of the P4 indicator cells on day 3; colorimetric revelation of the assay is performed on day 5.

Table II shows the results of protease inhibitor susceptibility testing following this schedule in 8 patients of which 2 were protease inhibitor naive and 6 were showing signs of escape to protease inhibitor treatment.

TABLE II

Protease Inhibitors IC 90 Values Measured On Clinical Plasma Samples

| Patient # | Treatment | Protease Genotype | IC90 | | | |
|---|---|---|---|---|---|---|
| | | | IDV | RTV | SQV | NFV |
| 1 | naive | wild-type | 14 | 35 | <5 | 25 |
| 2 | Saquinavir | L10I, M46I, G73S, L90M | 242 | 537 | 51 | 624 |
| 3 | Indinavir | L10I, K20R, V82A | 968 | 856 | 10 | 100 |
| 4 | Saquinavir, Indinavir | F53L, A71V, G73S, L90M | 453 | 533 | 109 | 592 |
| 5 | Ritonavir | K20R, M36I, I54V, V82A | 776 | 997 | 7 | 369 |
| 6 | Saquinavir | L10I, M36I, A71V, 184V, L90M | 199 | 272 | 63 | 243 |
| 7 | naive | L63H | 18 | 37 | <5 | 55 |
| 8 | Saquinavir | A71T, L90M | 258 | 719 | 72 | 1055 |

The IC90 values were calculated using the method of Chou et al. from the mean colorimetric OD values measured in triplicate assays. Both protease inhibitor-naive patients had comparable, low IC90 values regarding all five protease inhibitors tested. Consistent with previous reports, the SQV IC90 of pretherapy recombinant viruses was always significantly lower than with the other protease inhibitors.

The 6 post-escape viruses presented on Table II display a significant increase in IC90 regarding most of the protease inhibitors tested. However, this cross-resistance was not absolute. Indeed, all 4 viruses carrying protease sequences from patients treated with SQV had a prominent increase of their SQV IC90, while the two other viruses, from patients treated by RTV or IDV, revealed a more modest resistance to SQV. Interestingly, these two viruses lacked the L90M mutation that is mostly characteristic of resistance to SQV.

A further evaluation of HIV-1 cross-resistance to protease inhibitors using the single-cycle recombinant assay of the invention was conducted in 4 patients that had followed distinct treatment regimens (FIG. 3). For each patient, the susceptibility of the post-escape virus is presented as an increase in IC90 compared with parental pretherapy virus from the same patient.

As shown on FIG. 3, the RTV escape in patient 1 (with mutations K20R, M36I, I54V, and V82A) was characterized by a significant increase in IC90 to RTV, IDV and nelfinavir (NFV), while the virus appeared to retain wild-type susceptibility to SQV and amprenavir (AMP). IDV-escape virus from patient 2 (mutations L10I, K20R, and V82A) was mostly resistant to RTV and IDV, marginally resistant to NFV and VX, and sensitive to SQV. Escape virus from patient 3, who had received IDV followed by an association of RTV and SQV (mutations: L10I, M46I, G73S, and L90M), had a broad cross-resistance to all 5 of the protease inhibitors tested. Escape virus from patient 4, obtained after successive treatments with SQV, IDV, and RTV associated to SQV, was found with the rare F53L mutation in a minor population of genomes and with mutations A71V, G73S, and L90M. This virus also displayed a broad cross-resistance to all 5 protease inhibitors.

The single-cycle resistance assay of this invention can readily evaluate HIV resistance and cross-resistance patterns. The results using this assay are consistent both with the genotypes of the corresponding virus and with the treatment history of the patients.

Detailed procedures for carrying out the assay of the invention are provided in the following Examples.

EXAMPLE 1

PCR Amplification

HIV protease sequences were amplified from patient plasma virus by nested RT-PCR. The first round of RT-PCR was conducted with the ProA+/ProA− primers pair.
Primer ProA+: 5'GCTAATTTTTTAGGGAAGATCTG3' (SEQ. ID NO. 1), spans the pNL4-3 sequence between positions 2080 and 2102.
Primer ProA−: 5'GGCAAATACTGGAGTATTGTATG3' (SEQ. ID NO. 2) extends from 2725 to 2703 of pNL4-3.

The second round of nested PCR was conducted with the ProB+/ProB− primers pair.
Primer ProB+: 5'TTTTTAGGGAAGATCTGGCCTTC3' (SEQ. ID NO. 3), extends from 2086 to 2108, while primer ProB−: 5'GGAGTATTGTATGGATTTTCAGG3' (SEQ. ID NO. 4), extends between positions 2735 and 2713 of pNL4-3.

The resulting nested PCR product has a size of 639 base pairs. It contains 166 base pairs of HIV-1 sequences located upstream of the protease coding region and extends 175 base pairs beyond the end of the protease. The nested PCR products were analyzed for their size and purity by agarose gel electrophoresis, purified on QiaAmp columns, and kept frozen until used.

The nucleotide sequence of the protease coding region was determined by automated dideoxynucleotide chain termination sequencing on the bulk nested PCR products using the following primers:

PRO1 (plus-strand) 5'CCCTCTCAGAAGCAGGAG3' (SEQ. ID NO. 5); and

PRO2 (minus-strand) 5'TGGGCCATCCATTCCTGGCT3' (SEQ. ID NO. 6).

EXAMPLE 2

Plasmid Identity and Manipulation

The HIV-1 molecular clone used in this Example was derived from plasmid pNL4-3. A complete XbaI-ClaI deletion of the protease coding sequence was achieved in pNL4-3XC, a previously described modification of pNL4-3. See Patick et al., J. Virol., 69:2148–2152.

The deleted protease sequences were replaced by a double-stranded synthetic linker composed of oligonucleotide MLU1 (5'CTAGACGCGT3') (SEQ. ID No. 7) annealed to oligonucleotide MLU2 (5'CGACGCGT3') (SEQ. ID NO. 8), creating plasmid pNLXC-Mlu with a unique MluI site in place of the deletion. The presence of this unique MluI site in the plasmid allowed simple plasmid linearization at the site of the protease deletion by MluI digestion.

The next step was to ensure that no HIV-1 envelope could be expressed by the HIV-1 molecular clone used in the recombination experiments. In order to construct a plasmid with both a protease and env deletion, a 4.2 kb fragment containing the whole gag and pol coding sequences between position 1507 and position 5745 in pNL4-3 was extracted from plasmid pNLXC-Mlu by SpeI and EcoRI digestion. This DNA fragment was cloned into the SpeI-EcoRI digested pNLenv- plasmid, a previously described pNL4-3-derived plasmid carrying a near full deletion of the env gene. Clavel et al., J. Virol., 63:1455–59 (1989). The resulting protease-deleted and envelope-deleted plasmid, pNLME, was subsequently used in the recombination experiments.

Expression of the VSV-G envelope glycoprotein in transfected cells was ensured by a plasmid, which contains the VSV-G coding sequence under the control of the CMV promoter.

EXAMPLE 3

Cell Culture Techniques

HeLa cells and P4 cells were cultivated in DMEM. All cultures were supplemented by 10% FCS and antibiotics. P4 cells are HeLa-CD4, LTR-LacZ cells in which the expression of β-galactosidase is strictly inducible by the HIV transactivator protein Tat, thereby allowing precise quantitation of HIV-1 infectivity based on a single cycle of replication. P4 cells were cultured in the presence of 500 μg/ml geneticin.

EXAMPLE 4

Protease Inhibitor Resistance Assay of the Invention

Subconfluent HeLa cultures in 24-well plates were transfected with a mixture of 1.33 μg of MluI-digested, linearized pNLME, 0.33 μg of VSV-G plasmid, and 0.2 μg of protease PCR product amplified from patient plasma. Transfection was achieved following the calcium phosphate precipitation method.

After 24 hours, the transfected HeLa cells were washed and treated with increasing concentrations of protease inhibitor (0, 1, 5, 25, 125, 625, 3125 nM). After 24 hours of treatment, 3×100 microliters of viral supernatant from each culture were used to infect triplicate subconfluent P4 cells, cultured in 96-well plates, in the presence of 60 μg/ml of DEAE-dextran. Twenty-four hours after infection of P4 cells, the single cycle titer of viruses produced in the presence of the inhibitor was determined by quantification of the β-galactosidase activity in P4 lysates using a calorimetric assay based on cleavage of chlorophenol red-β-D-galactopyranoside (CPRG) by β-galactosidase (adapted from Eustice et al., BioTechniques, 11:739–743 (1991)). Briefly, following elimination of the supernatant, the P4 cells were lysed in 100 μl of lysis buffer ($Na_2HPO_4$.60 mM, $NaH_2PO_4$ 40 mM, KCl 10 mM, $MgSO_4$ 10 mM, EDTA 2.5 mM, β-mercaptoethanol 50 mM, NP40 0.125%) After incubation for 5 min at room temperature, 100 μl of reaction buffer (Phosphate buffer (Na) pH 7.4 8 mM, $MgCl_2$ 10 mM, β-mercaptoethanol 10 mM, CPRG 6 mM) were added to the cell lysates and incubated from 1 minute to 2 hours at 37° C. Colorimetric reactions were irreversibly arrested by freezing the plates at −80° C. for at least 2 hours.

Optical densities in the reaction wells were read at 570 nm with a reference filter set at 690 nm. The IC50 and IC90 calculations were performed according to the method of Chou et al., Adv. Enz. Regul., 22:27–55 (1984).

Based upon the foregoing description, it will be evident that this invention includes kits for caring out the assay of the invention. The kit includes primers for reverse transcriptase-PCR or an equivalent technique using nucleotide sequences as probes, a deleted proviral plasmid clone, P4 cells for culture, HeLa cells as producer cells, and sensitive and resistant internal controls. The kit can also include reagents for cell transfection and reagents for detecting, such as the reagents necessary for beta-galactosidase quantification.

In summary, a variety of assays are currently being developed for the evaluation of HIV drug resistance. Genotypic assays detect the presence of resistance mutations in the genes coding for HIV protease or RT. Most of the resistance mutations that can arise in the course of antiretroviral therapy of HIV infection are now well identified. Although some mutations appear to be specific to one particular antiretroviral, many others have been found associated with treatment by several different drugs. This latter case is particularly true for resistance to protease inhibitors. Moreover, with the widespread use of antiretroviral combination therapy, the genotypic profiles of HIV-1 variants escaping treatment tends to be more and more complex and degenerate, making it difficult to precisely evaluate to which drugs the corresponding viruses may be fully resistant and to which drugs they may retain some level of susceptibility. In these cases, the presence and the accumulation of resistance mutations can certainly constitute a good marker of the evolution of resistance, but cannot be used to quantitatively evaluate the level of resistance, a parameter that could reveal crucial to optimizing therapeutic orientations in patients who fail antiretroviral therapy.

Phenotypic resistance assays aim at directly measuring susceptibility of HIV in tissue culture. The first described phenotypic assays for HIV were conducted in primary isolates that first had to be isolated from patient blood cells by cocultivation with PHA-stimulated peripheral blood lymphocytes (PBLs) from normal donors. Because they required virus isolation and titration before the actual testing procedure, these assays have proven highly time and labor consuming. Virus isolations on PBLs require one to two weeks and often fails because of low virus load in the studied blood samples. Moreover, since the procedure needs to be carried out on primary donor cells that often exhibit different susceptibilities to HIV replication, and since primary HIV isolates can differ in their cell tropism and replicative capacity, standardization of such assays has proven difficult.

An innovative alternative to these assays was proposed by Kellam and Larder in 1994. Their assay, termed RVA, measures resistance of a recombinant virus carrying RT from patient plasma within a laboratory isolate genome backbone. HIV laboratory isolates are competent for replication in a variety of established cell lines. Similar to the assay of this invention, the initially described RVA method involved cotransfection between HIV sequences from patient samples and a deleted HIV laboratory molecular clone. However, because the efficiency of transfection and recombination in lymphoid cell lines was low, the virus produced by the transfected cells had to be amplified by propagation in lymphoid cells, a process that requires accumulation of multiple rounds of virus replication. In such a system, the virus is subjected to selection and genetic drift before being tested for resistance. Therefore, key resistance mutations that may affect virus fitness can be lost, and the measured resistance values may not reflect those of the authentic clinical virus.

In addition, the recombinant virus can carry a genome that is defective for envelope expression, preventing propagation and possible selection of this virus in the transfected HeLa cells and in the P4 indicator cells. Therefore, resistance is measured on the basis of a single cycle of replication, which ensures rapid testing and discards the risk of any genetic drift of the virus during the testing procedure.

Many published HIV resistance assays rely on measurement of virus-mediated cytopathic effect (CPE) for the calculation of the resistance values. In the cell systems used for these assays, the development of CPE over time is largely a function of virus input. Therefore, standardization of these assays requires careful titration of the virus stocks that are subjected to inhibition by the drugs.

What is claimed is:

1. An in vitro, single cycle, recombinant virus assay (RVA) for determining HIV susceptibility to protease inhibitor, wherein the method comprises:

(A) transfecting a human epithelial cell line with,
(1) amplified HIV protease sequences of an HIV virus to be assayed for resistance to the protease inhibitor;
(2) an HIV, envelope defective, molecular clone for recombination, wherein the molecular clone has a complete deletion of its protease coding sequence and an envelope deletion so that no HIV envelope is expressed by the HIV molecular clone; and
(3) a plasmid containing VSV-G envelope coding sequence under the control of a promoter for phenotypic complementation of the HIV, envelope defective, molecular clone;

(B) culturing the resulting transfected cells to repair the protease coding sequence by homologous recombination between the HIV molecular clone and the amplified HIV protease sequences, and to produce a testable stock of infectious particles by coexpression of the protease-repaired HIV molecular clone and the VSV-G envelope coding sequence;

(C) contacting cells of the culture from step (B) with the protease inhibitor;

(D) infecting indicator cells containing an indicator gene with the testable stock of infectious particles from step (C), without amplification of the infectious particles prior to infecting the indicator cells;

(E) expressing the indicator gene in the indicator cells from step (D); and (F) determining accumulation of indicator gene product as a measure of inhibition of HIV replication by the protease inhibitor.

2. The assay as claimed in claim 1, wherein the HIV protease sequences are from patient plasma virus.

3. The assay as claimed in claim 1, wherein the HIV, envelope defective, molecular clone is linearized at the locus of the deletion of the protease coding sequence.

4. The assay as claimed in claim 1, wherein the HIV, envelope defective, molecular clone has a complete deletion of its envelope coding sequence.

5. The assay as claimed in claim 1, wherein the human epithelial cell line comprises HeLa cells.

6. The assay as claimed in claim 1, wherein viral particles are assembled and released from the cells cultured in step (B).

7. The assay as claimed in claim 1, wherein the protease inhibitor is selected from the group consisting of saquinavir, indinavir, ritonavir, nelfinavir, amprenavir, and mixtures thereof.

8. The assay as claimed in claim 1, wherein the indicator cells comprise cells containing sites of early steps of HIV replication comprising virus entry, reverse transcription, nuclear import of viral DNA, integration, and expression up to the production of sufficient amounts of Tat transactivator for accumulation of detectable amounts of the indicator gene.

9. The assay as claimed in claim 1, wherein the indicator gene is β-galactosidase.

10. The assay as claimed in claim 1, wherein the indicator cells are P4 cells.

11. The assay as claimed in claim 1, wherein the HIV protease sequences have been amplified by PCR.

12. The assay as claimed in claim 1, wherein the envelope coding sequence encodes VSV-G envelope glycoprotein.

13. The assay as claimed in claim 1, wherein the cells of the culture from step (B) are contacted with serial dilutions of the protease inhibitor.

14. The assay as claimed in claim 1, wherein the amplified HIV protease sequences of the HIV virus to be assayed comprise at least about 100 base pairs of HIV sequences located upstream of the protease coding sequence, and at least about 100 base pairs of HIV sequences located beyond the end of the protease coding sequence for homologous recombination.

15. An in vitro, single cycle, recombinant virus assay (RVA) for determining inhibition of HIV replication by a protease inhibitor, wherein the method comprises:

(A) transfecting a human epithelial cell line with,
(1) amplified HIV protease sequences from patient plasma;
(2) an HIV, envelope defective, molecular clone for recombination, wherein the molecular clone has a complete deletion of its protease coding sequence and an envelope deletion so that no HIV envelope is expressed by the HIV molecular clone; and
(3) a plasmid containing VSV-G envelope coding sequence under the control of a promoter for phenotypic complementation of the HIV, envelope defective, molecular clone;

(B) culturing the resulting transfected cells, in the presence of the protease inhibitor, so that the protease coding sequence is repaired by homologous recombination between the HIV molecular clone and the amplified HIV protease sequences, and to produce a testable stock of infectious particles by coexpression of the repaired HIV molecular clone and the HIV envelope coding sequence;

(C) infecting indicator cells containing an indicator gene with the testable stock of infectious particles from step (B), without amplification of the infectious particles prior to infecting the indicator cells; and (D) determining accumulation of indicator gene product in the indicator cells as a measure of inhibition of HIV replication by the protease inhibitor.

16. The assay as claimed in claim 15, wherein the HIV, envelope defective, molecular clone is linearized at the locus of the deletion of the protease coding sequence.

17. The assay as claimed in claim 16, wherein the HIV, envelope defective, molecular clone has a complete deletion of its envelope coding sequence.

18. The assay as claimed in claim 17, wherein the human epithelial cell line comprises HeLa cells, the indicator gene is β-galactosidase, and the envelope coding sequence encodes VSV-G envelope glycoprotein.

* * * * *